United States Patent
Lee et al.

(10) Patent No.: US 7,408,365 B2
(45) Date of Patent: Aug. 5, 2008

(54) IMAGE SENSOR TESTING METHOD AND APPARATUS

(75) Inventors: Jongmoon Lee, Gyeonggi-do (KR); Juntaek Lee, Gyeonggi-do (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 0 days.

(21) Appl. No.: 11/486,106

(22) Filed: Jul. 14, 2006

(65) Prior Publication Data

US 2007/0159190 A1 Jul. 12, 2007

(30) Foreign Application Priority Data

Jan. 9, 2006 (KR) .............. 10-2006-0002296
Mar. 9, 2006 (KR) .............. 10-2006-0022314

(51) Int. Cl.
 *G01R 31/302* (2006.01)
(52) U.S. Cl. ..................................... 324/752
(58) Field of Classification Search .............. 324/158.1, 324/750–762; 382/149, 274
 See application file for complete search history.

(56) References Cited

U.S. PATENT DOCUMENTS

| 3,796,947 | A | * | 3/1974 | Harrod et al. ............... 324/501 |
| 4,730,158 | A | * | 3/1988 | Kasai et al. .................. 324/751 |
| 4,788,495 | A | * | 11/1988 | Plies ........................... 324/751 |
| 5,493,236 | A | * | 2/1996 | Ishii et al. .................... 324/752 |
| 6,038,038 | A | * | 3/2000 | Selby et al. .................. 358/446 |
| 6,731,122 | B2 | * | 5/2004 | Feng ............................ 324/752 |
| 6,765,396 | B2 | * | 7/2004 | Barror ......................... 324/753 |
| 6,900,887 | B2 | * | 5/2005 | Kim ............................. 356/218 |
| 6,906,332 | B2 | * | 6/2005 | Tashiro et al. .......... 250/370.11 |
| 7,085,408 | B1 | * | 8/2006 | Chung-Chi Jim ........... 382/149 |
| 7,123,298 | B2 | * | 10/2006 | Schroeder et al. ........... 348/273 |
| 7,148,715 | B2 | * | 12/2006 | Akram et al. ................ 324/765 |
| 2005/0083073 | A1 | * | 4/2005 | Nihei et al. .................. 324/758 |

FOREIGN PATENT DOCUMENTS

| JP | 06-244396 | | 9/1994 |
| JP | 10340349 | A | 12/1998 |
| JP | 2002-164526 | | 6/2002 |
| JP | 2003279463 | A | 10/2003 |
| JP | 2005091209 | A | 4/2005 |
| KR | 1020020097336 | | 12/2002 |
| KR | 1020050085408 | A | 8/2005 |

* cited by examiner

*Primary Examiner*—Ha Nguyen
*Assistant Examiner*—Joshua Benitez
(74) *Attorney, Agent, or Firm*—Volentine & Whitt, PLLC

(57) ABSTRACT

Disclosed are an optical test apparatus, related test method and method of operation, and related probe card adapted to optically test an image sensor. An illumination source of the optical test apparatus provides an optical test signal to the image sensor through the probe card. The optical test signal has a property variably defined by a feedback loop formed between a reference image sensor associated with the probe card and a control unit connected between the reference image sensor and the illumination source.

9 Claims, 7 Drawing Sheets

IMAGE SENSOR TESTING METHOD AND APPARATUS

BACKGROUND OF THE INVENTION

1. Field of the Disclosure

Embodiments of the invention relate generally to image sensor testing methods and related testing apparatuses. More particularly, embodiments of the invention relate to automated test methods for image sensors and related test apparatuses providing improved testing uniformity.

This application claims the priority of Korean Patent Application Nos. 2006-0002296, filed Jan. 9, 2006, and 2006-0022314, filed Mar. 9, 2006, the disclosures of which are hereby incorporated by reference in their entirety.

2. Description of the Related Art

Improved semiconductor fabrication technology has resulted in semiconductor image sensors characterized by smaller size, high quality performance, and lower manufacturing costs. As a result, image sensors are now used in a wide variety of commercial devices, such as digital cameras, camcorders, printers, scanners, and certain cellular telephones. In general operation, image sensors are adapted to capture optical energy (e.g., visible light), convert the optical energy into coherent electrical signals, and subsequently process the electrical signals into digital data that may be easily stored, transferred, and manipulated. The end result of this remarkable sequence of processes is the generation of image data that may be visually displayed or recorded in a number of different forms using conventionally available digital media.

The two most widely used types of semiconductor image sensors are the charge coupled device (CCD) and the CMOS image sensor (CIS). CCD sensors generally provide higher performance than CIS sensors. CCD sensors operate with comparatively lower noise and higher device uniformity. However, CIS sensors operate with comparatively lower power consumption and at higher operating speeds. The lower power consumption and higher operating speed provided by CIS sensors make CIS sensors the image sensor of choice for many portable electronic devices. That is, for many portable electronic devices constrained in their design and operating characteristics by a limited battery life, the reduced power consumption is an acceptable trade-off with the inferior performance of CIS sensors relative to CCD sensors. Cellular telephones having an integrated camera are one example of this type of portable electronic device.

This current design preference related to portable electronic devises raises some difficult challenges in the context of the constituent image sensors. For example, given the inherent weaknesses associated with CIS sensors (e.g., high noise and less uniformity between individual sensor operations), the quality control and testing processes within the lengthy sequence of fabrication processes necessary to manufacture CIS sensors become increasingly important.

Regardless of whether CCD or CIS technology is used, most image sensor manufacturers begin quality control testing at the wafer level to avoid the expense of continued fabrication of failed image sensor elements, and to reduce the possibility of producing non-functional or substandard products. The term "wafer level" refers to any fabrication process, including testing and quality control processes, performed on a wafer substrate containing many individual semiconductor image sensors. (See, Figure (FIG.) 1). Wafer level testing is performed before individual devices are cut from the wafer and packaged or connected to other host device components.

Given the optical-to-electrical conversion functionality provided by image sensors, it is not surprising that optical testing (e.g., a test associated with the optical illumination of the image sensor) is an important part of the overall quality control process. A great deal of optical testing is performed at the wafer level. Such testing directly implicates the quality of the optical test equipment and, more particularly, the quality of the illumination source within the optical test equipment. Indeed, the reliability of the optical test equipment should at all times exceed the performance specifications of the image sensors being tested. A consequence of this conclusion requires that the illumination source within optical test equipment be precisely controlled in its characteristics (e.g., intensity, wavelength, etc.), highly uniform in its application across a wafer, and very reliable. Without such qualities in an illumination source, it is impossible to distinguish performance variations between individual image sensors formed on the wafer.

As currently used in the fabrication of image sensors, conventional illumination sources are manually calibrated according to a periodic maintenance schedule (e.g., every 1000 to 2000 hours of operation). Such an approach requires interruptions of the fabrication process, as test equipment is taken off-line for maintenance. Further, the manual calibration process is subject to qualitative variations due to its inherent "human factors" (e.g., variations in the training of technicians, etc.).

Additionally, the mass production capabilities provided by modern semiconductor fabrication facilities mandates the use of multiple optical testing stations, each having an illumination source. Ideally, the illumination source used in each fabrication line should produce an identical output so that image sensor testing across multiple fabrication lines is consistent. Unfortunately, this is almost never the case. As presently instituted, each illumination source is merely tested (or compared) to a "standard" illumination source, and this process is inherently variable in its outcome.

The difficulty of consistently providing uniform, high quality illumination sources is compounded by the fact that the performance of all illumination sources tends to degrade over time. As a result, illumination source manufacturers provide expected performance profiles that characterize "typical" illumination performance over time. These performance profiles suggest voltage bias adjustments or operating voltage offset values for an illumination source during different periods of its life span. However, such performance profiles and the corresponding voltage offsets are merely "average" adjustments defined in relation to modeled outcomes. They do not accurately take into consideration the actual performance of individual illumination sources.

All of the foregoing results in an unacceptably high level of variation in the performance quality of illumination sources. Absent a reliable and clearly defined optical reference signal (e.g., uniform optical energy having a well controlled intensity) it is not possible to accurately characterize the performance of individual image sensors formed on a wafer. More critically, it is well understood that semiconductor fabrication processes frequently produce variable results across the surface area of a wafer (e.g., material layer characteristics on edge portions of the wafer verses center portions of the wafer). Such fabrication process variations must be identified, carefully quantified, and controlled in order to improve image sensor yield. It is nearly impossible to identify such process variations during wafer level optical testing of image sensors if the characteristics of the illumination source in the optical test equipment also vary across the surface of the wafer.

SUMMARY OF THE INVENTION

In one embodiment, the invention provides an optical test apparatus configured to test image sensors, and comprising; an illumination source adapted to generate an optical test signal having a property variably defined in relation to a control signal, a probe card adapted to pass the optical test signal through an exposure aperture to selected image sensors formed on a wafer associated with the probe card, the probe card comprising a reference image sensor disposed proximate the exposure aperture and adapted to generate an optical feedback signal in response to the optical test signal, a control unit adapted to receive the optical feedback signal and generate a control feedback signal in response to the optical feedback signal, and an operating unit adapted to receive the control feedback signal and generate the control signal.

In another embodiment, the invention provides an optical test apparatus configured to test image sensors, and comprising; an illumination source adapted to provide an optical test signal to an image sensor through a probe card, the optical test signal having a property variably defined by a feedback loop formed between a reference image sensor associated with the probe card and a control unit connected between the reference image sensor and the illumination source.

In yet another embodiment, the invention provides a method of operating an optical test apparatus adapted to wafer level test a plurality of image sensors formed on a wafer, the method comprising; controlling operation of an illumination source adapted to generate an optical test signal, the optical test signal having a property defined in relation to correlation table reference value data stored in memory, detecting the property of the optical test signal in relation to a probe card associated with the wafer and generating a corresponding optical feedback signal, comparing the optical feedback signal with at least one reference value in the correlation table, and rewriting at least one reference value in the correction table in response to the comparison.

In still another embodiment, the invention provides a method of operating an optical test apparatus adapted to test a plurality of image sensors formed on a wafer, the method comprising; defining a plurality of reference values in memory, illuminating selected image sensors in the plurality of sensors through a probe card with an optical test signal having a property variably defined in relation to the plurality of reference values, generating a feedback value corresponding to the optical test signal illuminating the selected image sensors, comparing the feedback value to one of the plurality of reference values to determine a difference, upon determining a difference, redefining at least one of the plurality of reference values in memory and compensating the optical test signal in relation to the at least one redefined reference values, and optically testing the selected image sensors in relation to the optical test signal.

In still another embodiment, the invention provides a probe card adapted for use in the testing of a plurality of image sensors formed on wafer, the probe card comprising; an exposure aperture adapted to pass an optical test signal to selected image sensors in the plurality of image sensors, at least one reference image sensor disposed proximate the exposure aperture, such that the at least one reference image is coincidentally illuminated with the optical test signal with the selected image sensors.

DESCRIPTION OF THE DRAWINGS

Several embodiments are described with reference to the accompanying drawings. It should be noted that various features in the drawings are not necessarily drawn to scale. In fact, the dimensions may be arbitrarily increased or decreased for purposes of clarity. Wherever applicable and practical, like reference numerals refer to like elements.

DESCRIPTION OF EMBODIMENTS

In the following description, for purposes of explanation and not limitation, embodiments of the invention are set forth to provide a more thorough understanding of the making and use of the invention. However, those of ordinary skill in the art having had the benefit of the subject disclosure will understand that other embodiments of the invention are possible. That is, numerous modifications and reconfigurations of the exemplary embodiments are possible without removing such from the scope of the appended claims. Moreover, descriptions of certain well understood aspects of the testing apparatus and related methods have been omitted for the sake of brevity.

Embodiments of the invention provide an optical testing apparatus incorporating higher quality illumination sources that provide an optical test signal (e.g., collimated light) having improved uniformity and precisely controlled characteristics. Embodiments of the invention provide related optical testing methods more capable of reliable performance discrimination between individual image sensors formed on a wafer. Embodiments of the invention allow highly accurate and uniform definitions of actual operating characteristics for multiple illumination sources being used in semiconductor fabrication facilities. Embodiments of the invention provide optical testing equipment and related methods of use that do not require routine human intervention to calibrate and verify the operating characteristics of an illumination source within the test equipment. As a result, the invention provides improved fabrication efficiency at reduced cost and greater testing reliability.

As used throughput this description the terms, "upper" and "lower", "above" and "below", "vertical" and "lateral", and similar expressions of relative disposition are intended to convey information regarding an exemplary relative orientation between two or more elements within the context of an embodiment. These terms should therefore be construed in a teaching context as being exemplary of all similar relationships. For example, merely flipping the relative orientation of two elements described as being above and below one another results in a similar relationship that merely reverses the above and below orientation of the elements. The actual implementation possibilities of the subject invention are limited to only the relative description of such elements as set forth hereafter.

Figure 1:
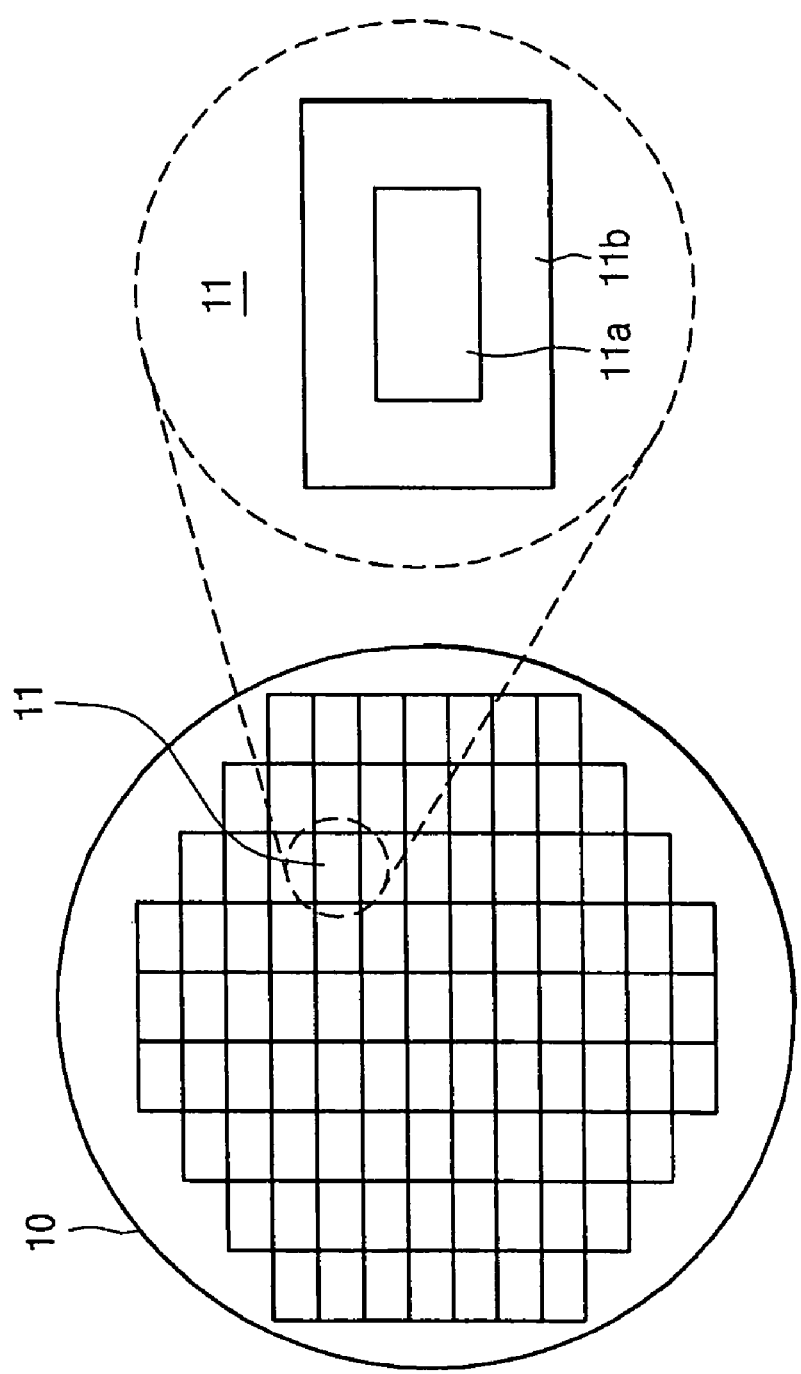
FIG. 1 illustrates a wafer containing a plurality of image sensors.

Embodiments of the invention find particular application, for example, in the testing of image sensors formed (or partially formed) on a wafer. FIG. 1 shows an exemplary wafer 10 containing a plurality of image sensors 11. Wafer 10 may be a silicon wafer such as those commonly used in the fabrication of conventional CCD or CIS sensors.

As shown in FIG. 1, the plurality of image sensors 11 may be arranged, as is common, in a series of rows and columns to efficiently fill the available surface area of wafer 10. Each image sensor 11 generally comprises an active pixel sensor (APS) array 11a and a peripheral circuit region 11b.

APS array 11a may be formed as a matrix of pixel elements arranged in rows and columns. In current conventional forms, each pixel comprises a photodiode (or a similar optically sensitive element) and an associated collection of connecting and support elements, such as a transfer transistor, a reset transistor, a selection transistor, a power supply transistor (e.g., a source-follower transistor), etc. Numerous specific designs for an APS array are understood by those of ordinary skill in the art.

Similarly, the layout and design of peripheral circuit region 11b will vary by application and enabling technologies, but as is conventionally understood, will typically comprise various digital circuits, such as a timing generator, a row decoder, a latch and column decoder, and so on. Further, peripheral circuit region 11b may also include various analog circuits, such as a correlated double sampler (CDS) and an analog to digital converter (ADC). Still further, peripheral circuit region 11b will typically include a number of electrical contact pads (not shown) adapted to connect image sensor 11 with external circuits. Some of these electrical contact pads have specific application during testing, as will be seen hereafter.

Figure 2:
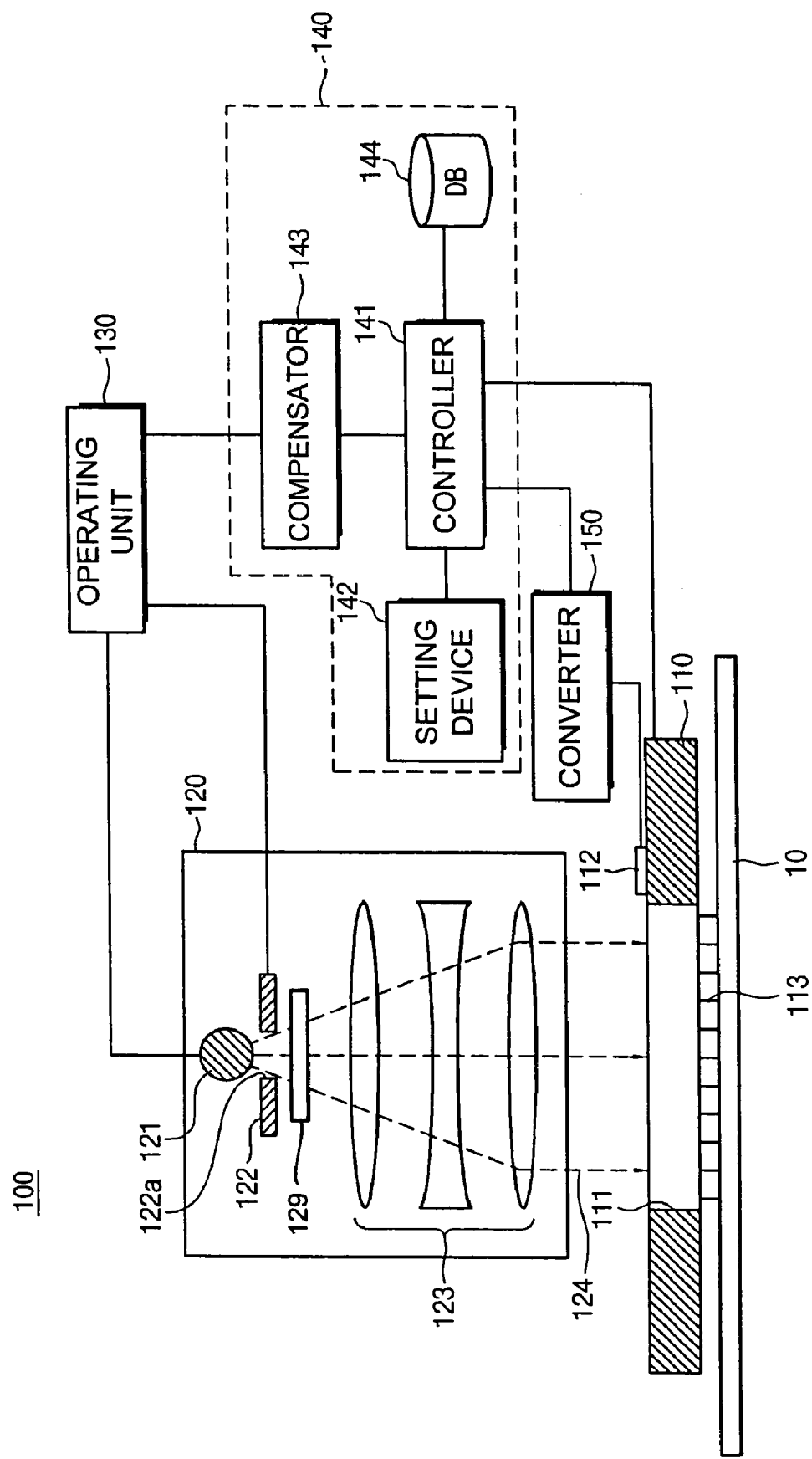
FIG. 2 is a schematic diagram illustrating an exemplary testing apparatus adapted to the testing of semiconductor image sensors according to one embodiment of the invention.

FIG. 2 depicts an exemplary optical testing apparatus 100 adapted to test a collection of image sensors at the wafer level during fabrication of the image sensors. In the illustrated example of FIG. 2, optical testing apparatus 100 comprises a probe card 110, an illumination source 120, an operating unit 130, a control unit 140, and a converter 150.

Probe card 110 comprises at least one exposure aperture (e.g., a slit shaped opening) 111 and at least one reference image sensor 112 located on an upper surface of probe card 110 proximate exposure aperture 111. In certain embodiments, reference image sensor 112 has the same or similar configuration as the image sensors being tested. As is conventionally provided, probe card 110 also comprises a number of electrical probes 113 extending from its lower surface. Electrical probes 113 are adapted for connection to electrical pads of individual image sensors formed on a wafer 10 seated under probe card 110.

Figure 4:
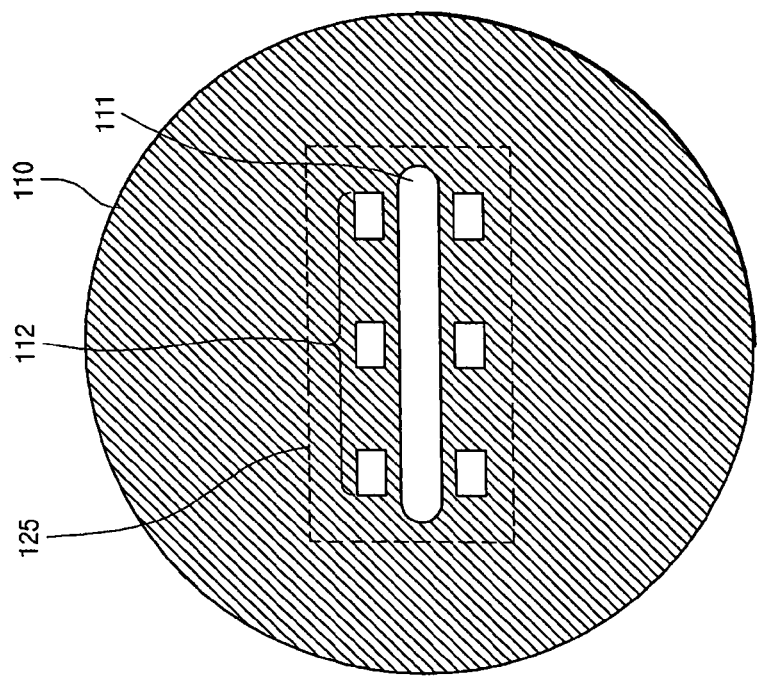
FIG. 4 depicts a second exemplary probe card adapted for use within the apparatus of FIG. 2.
Figure 3:
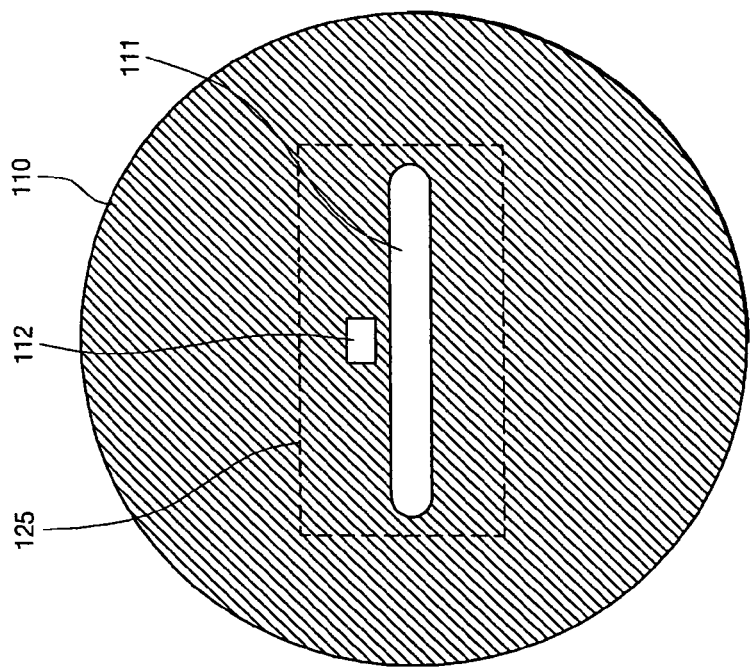
FIG. 3 depicts a first exemplary probe card adapted for use within the apparatus of FIG. 2.

FIGS. 3 and 4 further illustrate separate embodiments of a probe card 110 adapted for use in optical testing apparatus 100. As shown in FIG. 3, a centrally formed exposure aperture 111 is disposed in an illumination region 125 along with one reference image sensor 112. Illumination region 125 is a region defined in its size, shape, and orientation in relation to an optical test signal (e.g., collimated light 124) projected from illumination source 120 onto the upper surface of wafer 10 exposed onto selected image sensors through exposure aperture 111. In this regard, exposure aperture 111 may be defined in its size, shape, and orientation in relation to the size and number of image sensors to be tested during a given illumination step, a defined illumination region 125, and the characteristics of the optical test signal (e.g., the frequency, intensity, etc., of collimated light 124) projected by illumination source 120.

Use of probe card 110 according to an embodiment of the invention is similar in many respects to the use of a conventional probe card. For example, electrical probes 113 extending from probe card 110 may be used to provide power and test signals to input pads of the selected image sensors on wafer 10, and to receive corresponding output signals from output pads associated with the selected image sensors. Thus, as is conventionally understood, probe card 110 may be connected to an external tester or test station (not shown) in order to facilitate test signal communications between the selected image sensors and related test equipment. In this regard, the output of the reference image sensor(s) 112 positioned in probe card 110 may be similarly exported to related test equipment through connections provided by probe card 110. In certain embodiments of the invention, this related test equipment includes control unit 140 and converter 150, for example.

In FIG. 3, a single reference image sensor 112 is centrally disposed proximate exposure aperture 111 and within illumination region 125, while in FIG. 4, multiple reference images sensors 112 are arranged around exposure aperture 111. In some embodiments of the invention, additional reference image sensors 112 will provide a spatially-related, feedback reference gradient along and/or around exposures aperture 111. As compared with a single point of reference, such multiple points of reference will provide a more detailed indication of spatial variance in the characteristics of the optical test signal projected by illumination source 120.

In the illustrated example shown in FIG. 2, optical testing apparatus 100 positions illumination source 120 above probe card 110. In this position, illumination source 120 is well adapted to uniformly provide collimated light 124 as an optical test signal over the entire illumination region 125 of probe card 110. In the illustrated embodiment, illumination source 120 comprises a light source 121, a light aperture 122, a plurality of lenses 123, and one or more optical filters 129.

At this point, it should be noted that the term "light" as used throughout this description should be broadly construed to encompass optical energy of any reasonable wavelength or range of wavelengths. Thus, while visible light is highly relevant as an exemplary optical test signal in the context of contemporary commercial products, those of ordinary skill in the art will recognize that an optical test signal selectively comprising non-visible light (e.g., infrared or near-infrared light) might similarly be used within embodiments of the invention.

In a conventionally understood manner, the plurality of lenses 123 cooperates to collimate the light emitted by light source 121. Before reaching the plurality of lenses 123, however, the emitted light passes through light aperture 122. An opening size 122a for light aperture 122 may be adjustable under the precision control of operating unit 130. Thus, the intensity of collimated light 124 projected onto illumination region 125 by illumination source 120 to illuminate the selected image sensors being tested may be precisely controlled by varying light aperture size 122a.

In conjunction with the intensity variability provided by light aperture 122, one or more optical filters 129 may be used to further condition the emitted light. For example, one or more optical filters might be used to select-in or select-out certain optical wavelengths from the light emitted by light source 121. Provision of optical filters 129 allows the use of broad band light source 121, but also provides the ability to illuminate image sensors with a highly wavelength specific optical test signal.

Operating unit 130 may have a nominally conventional design, so long as this conventional design is further adapted (e.g., re-configured and/or re-programmed) to generate a control signal adapted to control the size 122a of light aperture 122. Indeed, many conventional optical test apparatuses include an operating unit adapted to generate an input voltage applied to light source 121. This input signal is generally a fixed voltage and may be feedback controlled within operating unit 130. However, the subject invention also contemplates embodiments wherein the input signal applied to light source 121 by operating unit 130 may be varied in relation to feedback and/or control signals provided by control unit 140.

With reference to the illustrated embodiment of FIG. 2, operating unit 130 may be further adapted to generate not only the input signal (e.g., a fixed or variable input voltage) controlling light source 121, but also a control signal adapted to control aperture size 122a. Various voltage controlled aperture mechanisms are generally available for this purpose. Further, the (re-) programming or reconfiguration of operating unit 130 for this purpose is deemed to be well within the ability of one of ordinary skill in the art.

In the illustrated embodiment, control unit 140 comprises a controller 141, a light intensity setting device 142, a compensator 143 and a data base 144. Controller 141 may be a conventional processor adapted for use in instrumentation and/or manufacturing equipment control applications. Compensator 143 may be a conventional digital data or analog signal comparator circuit. Light intensity setting device 142 may be a data register or data memory adapted to store reference data. If configured as a data memory, light intensity setting device 142 may be separately provided from database 144 or may be subsumed with database 144. Data base 144 may have any one of a number of conventional structures readily adapted to store one or more correction tables. The correlation tables may be used for multiple purposes, as described in some additional detail below.

Control unit 140, in addition to other functionality, is adapted to provide a feedback control signal to operating unit 130. It is this feedback control signal that defines the value of the control and/or input signal applied by operating unit 130 to light aperture 122 and/or light source 121.

Controller 141 may be further adapted to receive an optical feedback signal from reference image sensor(s) 112 through analog-to-digital converter 150, and send and/or receive test control and test data signals to/from probe card 110. Such test control and test data signals may be similar to those associated with conventional probe cards.

With continued reference to FIG. 2, an exemplary method of operation for optical testing apparatus 100 will now be described. The method begins when wafer 10, on which a plurality of image sensors has been formed or partially formed, is seated in relation to optical testing apparatus 100. Once seated in a testing position under probe card 110, selected image sensors are connected to electrical probes 113 and optically exposed through exposure aperture 111 in probe card 110. In this manner, selected image sensors may be serially tested in relation to collimated light 124 provided from illumination source 120. Following testing of one group of image sensors, probe card 110 and/or wafer 10 may be re-positioned to test another group of image sensors.

During optical testing, the selected image sensors are responsive to test control signals provided by controller 141 (and/or other test equipment) through electrical probes 113 and further responsive to collimated light 124 passing through exposure aperture 111. Under these inputs, individual image sensors output test data signals to controller 141 (and/or other test equipment). The output test data indicates the operating performance of the individual image sensors in relation to the test conditions, including the optical test signal provided by illumination source 120.

To ensure that the actual characteristics of the optical test signal provided by illumination source 120 is correct, reference image sensor(s) 112 associated with probe card 110 output an optical feedback signal through converter 150 to controller 141. The optical feedback signal (in analog or digital form) may be a voltage, current, frequency, and/or data value indicating reference image sensor(s) 112 response to the optical test signal (e.g., collimated light 124).

Before any actual testing of the image sensors on wafer 10 begins, control unit 140 initializes (or alternatively receives) a number of correction tables stored, for example, in database 144. The correction tables include reference data that allows control unit 140 to generate appropriate test control signals provided to probe card 110 and/or the control feedback signal provided to operating unit 130.

Figure 5:
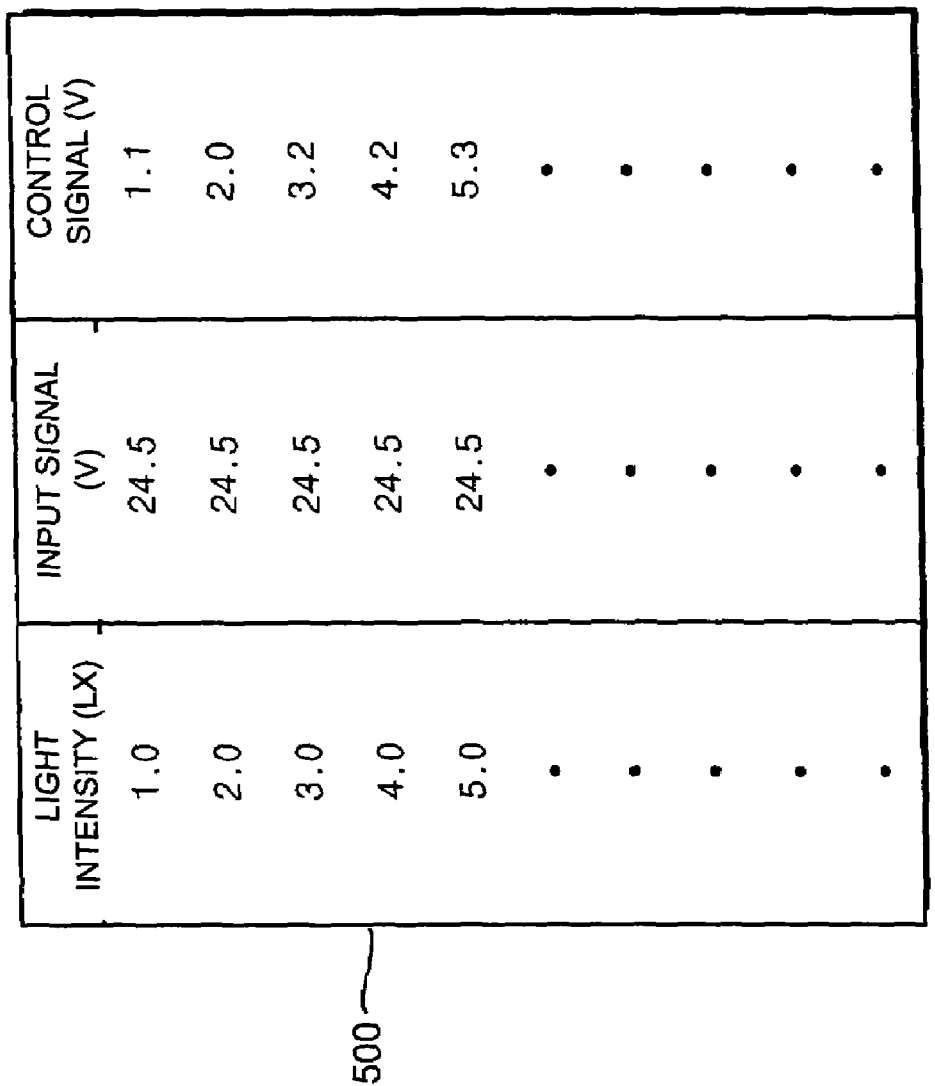
FIG. 5 depicts an exemplary correction table adapted for use in the control of the illumination source of FIG. 2.

FIG. 5 depicts an exemplary correction table 500. As shown in FIG. 5, correction table 500 comprises three columns of data. The data values in the first (leftmost) column respectively indicate desired light intensities for the optical test signal. The data values in the second column indicate an input signal applied to light source 121. In the illustrated example of FIG. 5, a fixed input signal is assumed. The data values in the third (rightmost) column respectively indicate control signals applied to control and light aperture size 122a. By varying the light aperture size 122a, the intensity of the optical test signal may be precisely controlled.

Under the influence of the feedback loop provided by reference image sensor(s) 112, control unit 140, and operating unit 130, illumination source 120 may be controlled by a control signal defined in relation to a specific value (or set of values) in correlation table 500. In one embodiment, the selected control signal value and/or the input signal value are provided as part of the control feedback signal provided to operating unit 130.

Additional correction tables may be provided that account for other testing criteria or influences, such as the age of light source 121, the ambient operating temperature, etc. Still further, in a configuration wherein light source 121 comprises multiple emitters (e.g., separate diodes providing a standard RGB output) separate correction tables may be created and maintained within database 144 to control the respective emitters.

Again returning to FIG. 2, once the appropriate correction tables have been accessed by controller 141, control unit 140 may issue an appropriately determined control feedback signal to operating unit 130. In response, operating unit 130 may control the output of an optical test signal by illumination source 120 in any number of ways, including the examples discussed above (e.g., controlling the input signal, the control signal, the selection of a filter, etc.), as well as other ways, including variable modulation of the input and control signals, varying an operating temperature, mechanical damping control, etc. Thus, under the control of operating unit 130, illumination source 120 is adapted to provide a well controlled, uniform optical test signal having defined properties to probe card 110 and the selected image sensors.

As collimated light 124 provided by illumination source 120 falls equally on reference image sensor(s) 112 and the selected image sensors being tested, real time feedback may be obtained regarding the actual properties of collimated light 124. Unlike the conventional optical testing apparatus, the illustrated embodiment of the invention is well adapted to track the actual intensity of collimated light 124 provided to the image sensors being tested. And this is true even at very low levels of the optical test signal. For example, the conventional test apparatus can not accurately assess an optical test signal at levels below about 1 lumen (lux). As a result an expensive piece of custom equipment has conventionally been brought to the optical test station in order to accurately assess the properties of an optical test signal at low levels. This extraordinary verification step is required since low light performance of the image sensors is an important performance criteria.

Figure 6:
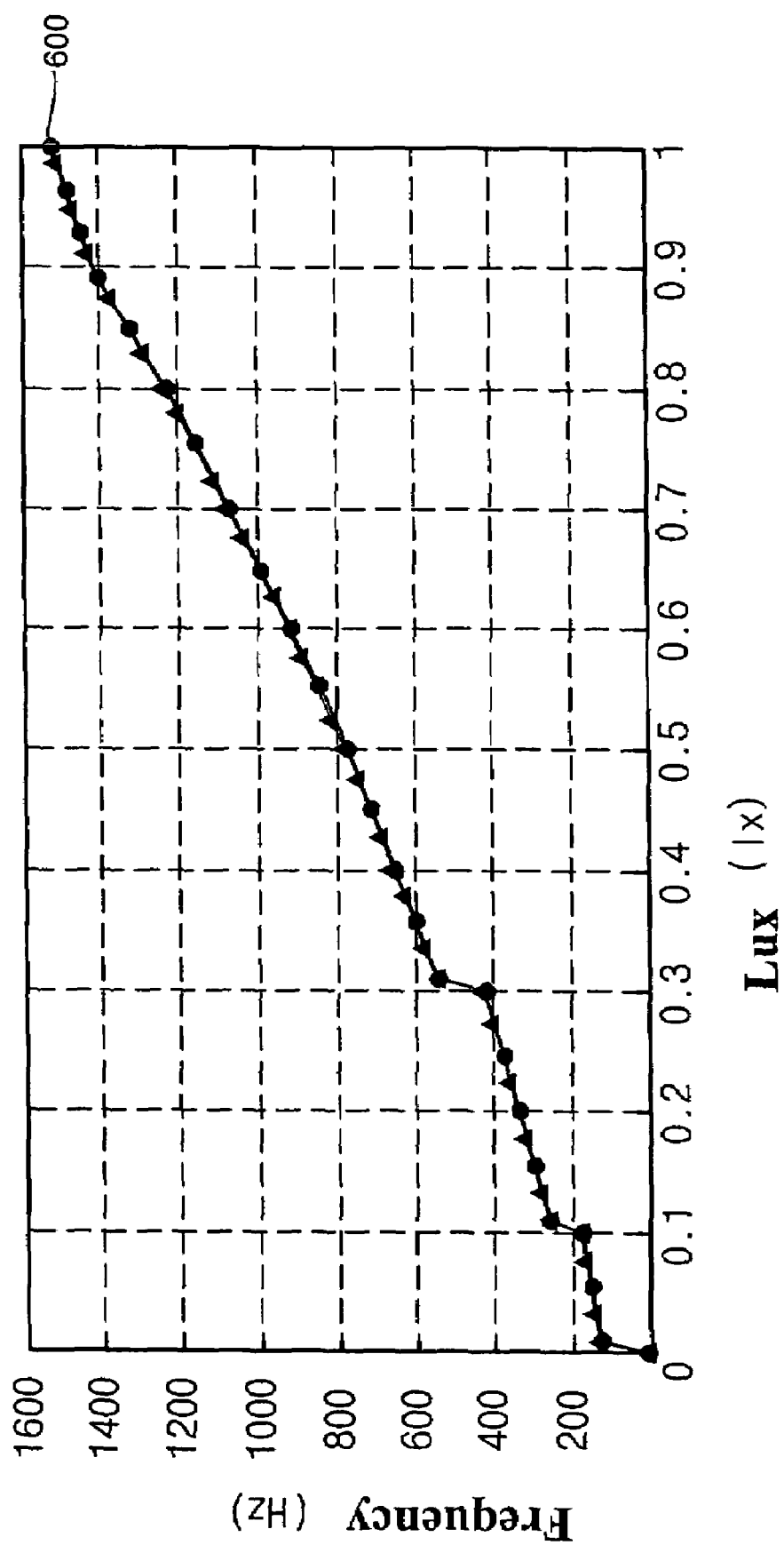
FIG. 6 is a graph showing a low light level transfer function for a reference image sensor according to an embodiment of the invention.

FIG. 6 is a graph depicting an exemplary transfer function 600 as indicated through a reference image sensor 112 associated with probe card 110. As shown, a range of luminescent power input from 0.0 to 1.0 lumens will cause reference image sensor 112 (e.g., via converter 150) to produce a frequency signal having a range between 0.0 hertz and about 1500 hertz. (Given the slight imperfections in the linearity of the exemplary transfer function 600, it may be advantageous in some embodiments to provide one or more feedback correction tables in database 144 to compensate for the linearity imperfections as such imperfections may degrade performance of optical test apparatus 100).

Nonetheless, the clarity of low light level feedback, as shown in FIG. 6, provided by the illustrated embodiment is remarkable. Very low intensity levels result in very fine output frequency distinctions which allow precise assessment of illumination source performance at the very low intensity levels. As a result, no specialized low light level test equipment is required and fabrication throughput is not interrupted in order to ascertain (or verify) the low light performance characteristics of the illumination source.

Again returning to FIG. 2, once controller 141 receives the optical feedback signal from reference image sensor(s) 112, it may compare the optical feedback signal (or a data value derived therefrom) to one or more reference values stored in light intensity setting device 142 or database 144 using compensator 143. In this regard, compensator 143 may be a hardware based comparator (e.g., a feedback adder circuit) or a software routine running on controller 141.

Should the reference value stored in light intensity setting device 142 be consistent with the received optical feedback signal, optical testing apparatus 100 may then perform any number of optical tests on the selected image sensors with a high degree of confidence in the test outcome. Various tests of interest may include overall sensitivity tests, low-light-level sensitivity tests, linearity tests, noise tests, tests for non-functional pixels, and so on. Single image sensors may be tested, multiple sensors may be tested, or in certain situations wafer 10 may be repeatedly repositioned to sequentially illuminate different rows of image sensors.

However, should the reference value stored in light intensity setting device 142 substantially differ from the received optical feedback signal, optical testing device 100 may be reconfigured, for example, by modifying the control feedback signal provided to operating unit 130. Such reconfiguration may involve incrementing or decrementing one or more reference values stored in a correlation table.

For example, should an optical feedback signal provided by reference image sensor(s) 112 indicate an actual optical test signal intensity (e.g. 1.9 lumens) that is 5% below a desired intensity level for the optical test signal (e.g., 2.0 lumens), control unit 140 may adjust an appropriate entry or entries in corresponding correlation table(s) to correct for this discrepancy. Thus, assuming table 500 shown in FIG. 5 as an example, the correction table entry for the control signal voltage corresponding to a desired light intensity of 2.0 lumens might be increased from 2.0V to 2.1V. This new correlation table entry would redefine the control feedback signal provided by control unit 140 to operating unit 130.

In this manner, real time feedback control over the actual optical test signal provided to the selected image sensors may be obtained. The foregoing description has been made in relation to light intensity as one exemplary property of the optical test signal. However, any one or more properties of the optical test signal generated by the illumination source, such as a frequency, wavelength, polarity, phase, modulation, etc., might be similarly controlled and compensated.

Further, the use of one or more stored correlation tables is but just one exemplary means by which one or more reference values (or reference signals) may be provided for use within the feedback control loop. In this regard, the terms "values" and "signals" as they relate to reference and feedback functionality may be interchangeably used, since those of ordinary skill in the art recognize that a value may be derived from a signal and a signal may be derived from one or more values.

Figure 7A:
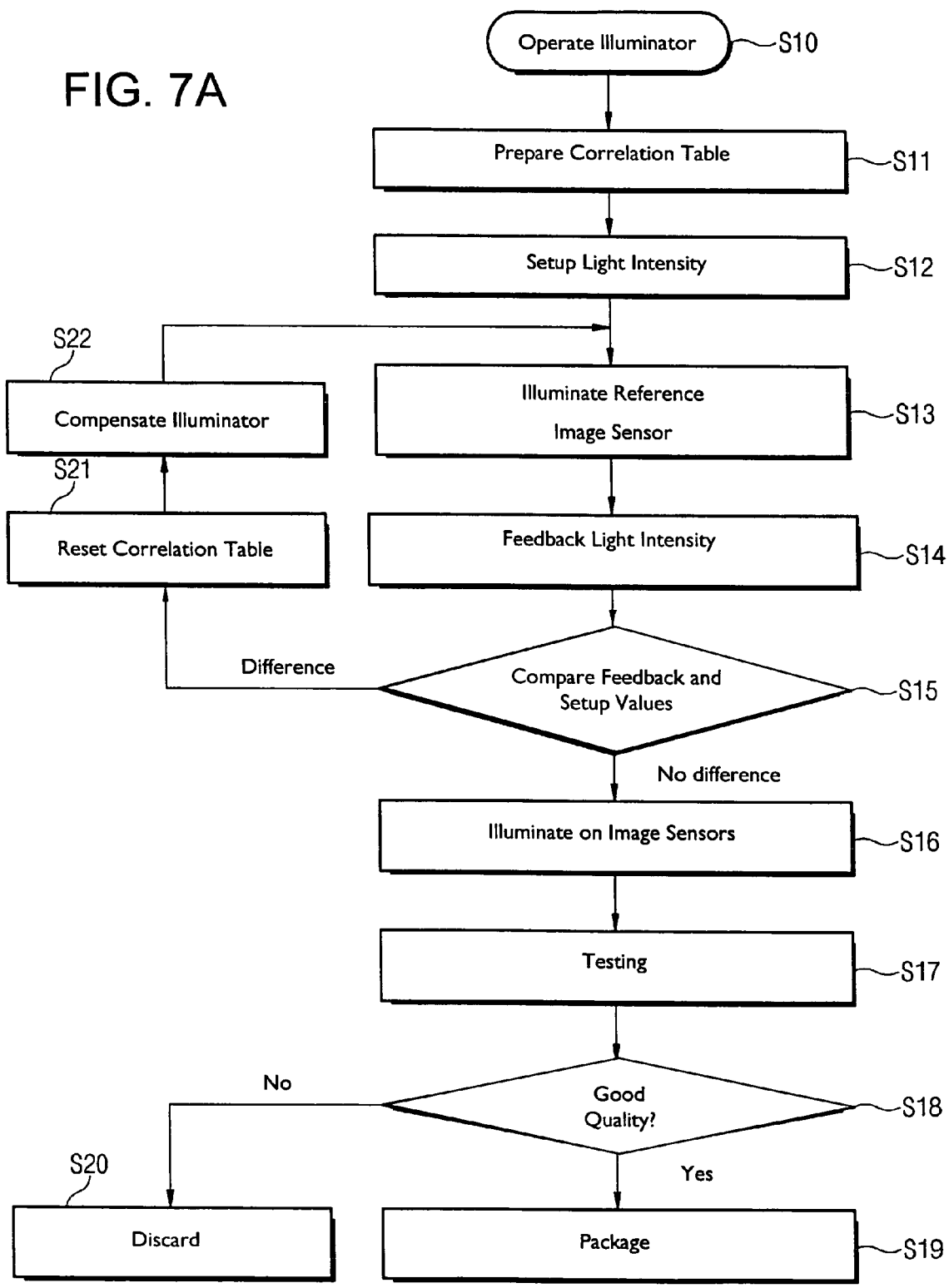
FIGS. 7A and 7B are flowcharts outlining exemplary methods of operation for the optical testing apparatus of FIG. 2.
Figure 7B:
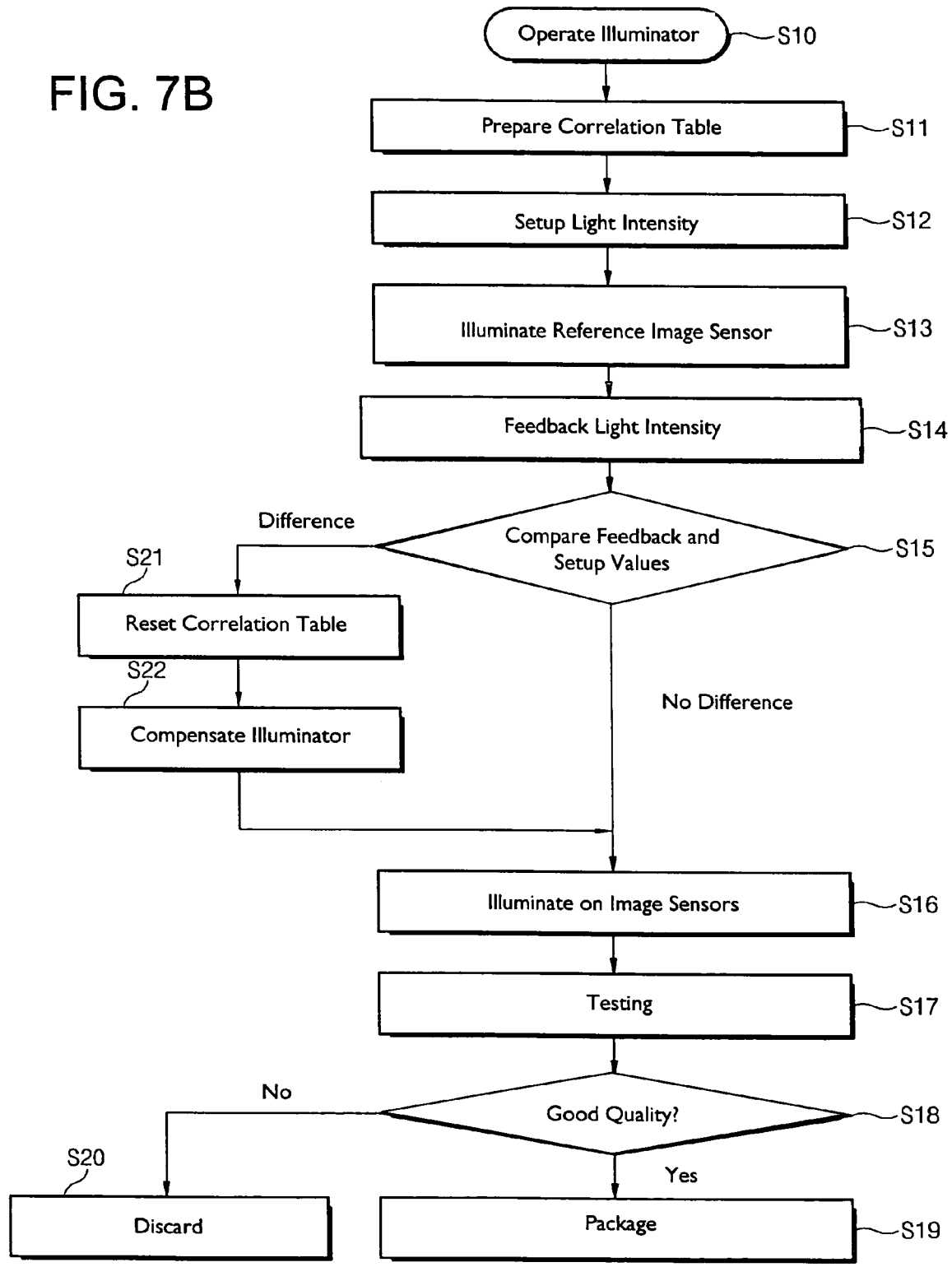

FIGS. 7A and 7B are flowcharts outlining exemplary methods of operation for the exemplary optical test apparatus 100. The methods of operation are drawn to the wafer level optical testing of image sensors. Intensity of the applied optical test signal is assumed as a feedback-controlled property.

With reference to the flowchart of FIG. 7A and the schematic illustration of FIG. 2, the exemplary method begins (S10) with an assumption that competent correction tables have been prepared and stored database 144 (S11). The correlation tables may take many forms (e.g., various data structures or data files) including, as an example, the form of correction table 500 shown in FIG. 5.

Next, based on one or more reference data values stored in the correlation tables, a desired optical test signal property is defined and set up within optical test apparatus 100 (S12). The "setup" procedure may involve reading the reference values from memory or receiving the reference values from an external source (E.g., a central computer system managing a fabrication facility), and then writing the reference data values into light intensity setting device 142 by means of controller 141.

With the optical test signal properties defined and setup within control unit 140, a control feedback signal may be provided to operating unit 130, which in turn provides an input signal and a control signal to illumination source 120. Under the influence of these "control" signals, illumination source 120 illuminates reference image sensor(s) 112 (S13).

Reference image sensor(s) 112 receive the optical test signal, convert it into a corresponding electrical signal and then pass the corresponding electrical signal to control unit 140 through converter 150. The corresponding electrical signal is an optical feedback signal indicative of the intensity of the optical test signal provided by illumination source 120 to reference image sensor(s) 112 (S14).

A feedback value may then be derived from the optical feedback signal using conventional techniques (e.g., sampling). Once derived, the feedback value is compared with the reference value stored, for example, in light intensity setting device 142. This comparison may be performed by controller 141 or compensator 143 to determine a potential difference between the feedback value and the setup reference value (S15). The difference or a lack of difference may then be used in the feedback loop to define further operation of the optical test apparatus 100.

If a material difference (a difference above a defined threshold) is determined, a correlation table entry (or set of entries) may be updated (e.g., rewritten in memory) in view of the determined difference (S21). Then based on the updated reference values stored in the correlation table, an updated control feedback signal may be defined and applied to operating unit 130 in order to adjust (or "compensate") the optical test signal output by illumination source 120 (S22). Following compensation, the illumination source 120 again illuminates the reference image sensor(s) 112 (S13) and the method of operation is returned to the primary execution path illustrated in FIG. 7A.

The compensation feedback loop provided by the exemplary method may be repeated until the properties of the optical test signal are verified. Of note, the compensation feedback loop may be repeated a number of times in relation to multiple properties of the optical test signal. That is, a first pass through the compensation feedback loop may compensate, as needed, for the intensity of the optical test signal, and a second pass through the compensation feedback loop may compensate for some other property.

Returning to FIG. 7A, if a material difference between the feedback value and reference setup value is not determined (S15), the selected image sensors to be tested are illuminated with the optical test signal (S16) and one or more optical tests are performed in relation to the optical test signal (S17). Optical testing is, thus, conducted with a very high degree of confidence, because the actual properties (e.g., intensity) of the optical test signal are known and accounted for by the provided feedback mechanism.

Based on the qualitative outcome of the optical testing (S18), the individual image sensors may be discarded as unacceptable (S20) or continue forward in the fabrication process towards packaging (S19).

The flowchart of FIG. 7B is very similar to that of 7A, except illumination of the image sensors (S16) occurs without performing the verification loop back through the steps of again illuminating the reference image sensor (S13) and again deriving a feedback value for the compensated optical feedback signal (S14). Instead, upon determining a difference between the feedback value and the reference setup (S15), the compensation steps (S21 and S22) are performed and then the image sensors are illuminated and tested (S16 and S17). This alternate method of operating optical test apparatus 100 is slightly more efficient (i.e., takes less time), but slightly less certain in its outcome, as the optical test signal is not verified following compensation before its actual use in testing.

In various embodiments where the above-described apparatus components and/or methods may be implemented using a programmable device, such as a computer-based system or programmable logic, it should be appreciated that the above-described apparatus and methods may be implemented using any of various known or later developed programming languages, such as "C", "C++", "FORTRAN", "Pascal", "VHDL" and the like.

Accordingly, various storage media, such as magnetic computer disks, optical disks, electronic memories and the like, can be prepared to contain information adapted to direct a general control device, such as a computer, to implement the some or all of the above-described functionality and/or methods in conjunction with a device adapted to project a competent optical test signal. Once such a general control device has access to the program and data contained on the storage media, it may perform some or all of the above-described functionality and/or method steps.

For example, if a computer disk containing appropriate program and data information, such as a source file, an object file, an executable file or the like, were provided to a computer, the computer could receive the information, appropriately configure itself and perform much of the functionality ascribed above to control unit 140 and operating unit 130, as well as implementing the methods outlined in the diagrams and flowcharts above. In this regard, the functionality of operating unit 130 and control unit 140 may be subsumed within a common hardware/software platform.

Many features and advantages of the invention are apparent from the foregoing description. It is intended that appended claims cover all such features and advantages that fall within the scope of the invention. Further, since numerous modifications and variations will readily occur to those skilled in the art, it is not desired to limit the invention to the exact construction and operation illustrated and described. But rather, all such modifications and equivalents fall within the scope of the invention.

What is claimed is:

1. A method of testing an image sensor formed on a wafer, wherein the wafer is associated with a probe card to facilitate communication of test control and test data signals to/from the image sensor, and the image sensor is tested in relation to an optical test signal, wherein the method comprises:

illuminating a reference image sensor disposed on the probe card with the optical test signal; and varying a property of the optical test signal in response to an optical feedback signal generated by the reference image sensor.

2. The method of claim 1, wherein the property of the optical test signal is intensity, and the method further comprises:

comparing the optical feedback signal with a reference value and on the basis of the comparison generating a control signal; and, applying the control signal to an illumination source generating the optical test signal.

3. The method of claim 2, further comprising:

storing a correlation table of reference values in memory;

selecting a reference value from the correlation table and generating the control signal in relation to the selected reference value.

4. The method of claim 3, further comprising:

rewriting a reference value in the correlation table in response to the comparison of the optical feedback signal with the reference value.

5. A method of operating an optical test apparatus adapted to test a plurality of image sensors formed on a wafer, the method comprising:

defining a plurality of reference values in memory;

illuminating selected image sensors in the plurality of sensors through a probe card with an optical test signal having a property variably defined in relation to the plurality of reference values;

generating a feedback value corresponding to the optical test signal illuminating the selected image sensors;

comparing the feedback value to one of the plurality of reference values to determine a difference, upon determining a difference, redefining at least one of the plurality of reference values in memory and compensating the optical test signal in relation to the at least one redefined reference values; and, optically testing the selected image sensors in relation to the optical test signal.

6. The method of claim 5, wherein optically testing the selected image sensors immediately follows compensation of the optical test signal.

7. A program configured to control operation of an optical test apparatus, the optical test apparatus being configured to test a plurality of image sensors disposed on a wafer in relation to an optical test signal passed to selected image sensors in the plurality of sensors though a probe card associated with the wafer, the program being executable on a controller associated with the optical test apparatus to implement a method, comprising:

controlling operation of an illumination source adapted to generate the optical test signal, the optical test signal having a property defined in relation to a reference value stored in a memory associated with the controller;

detecting the property of the optical test signal using the probe card and generating a corresponding optical feedback signal;

comparing the optical feedback signal with the reference value and redefining the reference value in response to the comparison.

8. The method of claim 7, wherein the property of the optical test signal is detected by a reference image sensor having a substantially similar configuration as the plurality of image sensors; and wherein the reference image sensor is disposed on the probe card such that the optical test signal coincidentally illuminates the reference image sensor and the selected image sensors.

9. The method of claim 8, further comprising:

optically testing the plurality of image sensors in relation to the optical test signal after redefining the correlation table.

* * * * *